United States Patent [19]

Wojciak

[11] 4,093,556

[45] June 6, 1978

[54] PROCESS FOR MICROENCAPSULATION OF METALLOCENES

[75] Inventor: Stanley Wojciak, New Britain, Conn.

[73] Assignee: Loctite Corporation, Newington, Conn.

[21] Appl. No.: 592,581

[22] Filed: Jul. 2, 1975

[51] Int. Cl.² ............................................. B01J 13/02
[52] U.S. Cl. .................................. 252/316; 252/182; 252/386; 252/431 R
[58] Field of Search ........................... 252/316, 431 R

[56] References Cited

U.S. PATENT DOCUMENTS 2,680,756   6/1954   Pauson ........................ 252/431 R X
3,516,941   6/1970   Matson ................................. 252/316
3,660,304   5/1972   Matsukawa ......................... 252/316

FOREIGN PATENT DOCUMENTS 989,264   4/1965   United Kingdom ................. 252/316

Primary Examiner—Richard D. Lovering
Attorney, Agent, or Firm—Jean B. Mauro; J. Rodney Reck

[57] ABSTRACT

A process for producing metallocenes encapsulated by a urea-formaldehyde polymer shell. The presence of a small amount of a cationic surfactant, preferably an alkyl hydroxy amine, is required during the condensation polymerization which forms the shell.

9 Claims, No Drawings

4,093,556

PROCESS FOR MICROENCAPSULATION OF METALLOCENES

BACKGROUND OF THE INVENTION

1. Field of the Invention

This invention relates to a process for encapsulating metallocenes by the in situ polymerization of urea and formaldehyde to form the capsule shell wells.

2. Prior Art

Microencapsulation of materials, whether solid, liquid or gas, is very well known in the art. More specifically, encapsulation of materials in durable shells of urea-formaldehyde has been described in U.S. Pat. No. 3,516,941 to Matson and, in a related case, British Pat. No. 989,264 in the name of Minnesota Mining & Mfg. Co. Insofar as relevant to the present invention, the disclosures of both those references are incorporated herein by reference. Microcapsule shell walls prepared by copolymerization of urea and formaldehyde are desirable for many applications because of their normally excellent toughness, i.e., resistance to premature breakage, and ability to resist leakage of the capsule contents. While the patents named above do provide instructions for the preparation of urea-formaldehyde shells, these instructions are not fully suitable for all materials. In particular, the procedures of those patents are not adequate for the encapsulation of that class of organic chemical compounds known as metallocenes.

SUMMARY OF THE INVENTION

The present invention relates to a process which improves upon the procedures of U.S. Pat. No. 3,516,941 and permits the satisfactory microencapsulation of metallocenes. Specifically, the present invention involves the use of a particular class of surfactants, namely, cationic surfactants, during the shell wall forming polymerization of urea-formaldehyde precondensates or prepolymers.

Accordingly, the present invention provides a process for microencapsulating a water-insoluble metallocene, a water-insoluble metallocene ion, or water-insoluble metallocene derivatives (e.g., polymers), or mixtures thereof, comprising:

(a) providing an aqueous solution of a water-soluble precondensate of urea and formaldehyde wherein the precondensate concentration is about 15 to about 50 percent by weight;

(b) adding to said precondensate solution a particulate metallocene in such amount that the weight ratio of metallocene to precondensate is between about 1:1 and about 8:1;

(c) adding to said precondensate solution or the mixture of said precondensate solution with said metallocene a cationic surfactant in such amount that the weight ratio of surfactant to metallocene is between about 1:6,000 and about 1:10;

(d) forming a slurry of the metallocene;

(e) adjusting the pH of the resultant dispersion to about 1 to about 6.5 by addition of a water-soluble acid, thereby causing polymerization of said precondensate; and (f) continuing said polymerization in the temperature range of about 15° to about 80° C. for at least about 1 hour, i.e., until said metallocene particles are encapsulated with a shell of water-insoluble urea-formaldehyde polymer.

DESCRIPTION OF THE PREFERRED EMBODIMENTS

The United States and British patents incorporated hereinabove by reference give, in considerable detail, the general procedures which should be followed in preparing urea-formaldehyde precondensates and microcapsules, so this detail need not be repeated here. The present invention differs essentially from the teachings of these references in that the present invention requires the use of a surfactant, specifically, a cationic surfactant or mixtures of such surfactants, in the encapsulation of particles of a metallocene or mixtures of metallocenes.

The metallocenes comprise a fairly common class of organo-metal compounds having the formula $(C_5H_5)_2M$, wherein M is a metal having a bonding capacity of at least 2. Typical of such compounds are ferrocene, n-butyl ferrocene, titanocene and cupricene. These compounds are typically in the form of friable solids and are not soluble in water.

These compounds find use in a variety of ways, e.g., catalysis, synthetic intermediates, anti-knock additives, etc. Of the metallocenes, perhaps the most useful, and the preferred one of this invention, is ferrocene, also known as dicyclopentadienyl iron. In addition to its other known uses, this material has recently been found useful as an accelerator for the cure of anaerobic adhesive and sealant compositions, such as those described in U.S. Pat. No. 3,855,040 to Malofsky. Encapsulation of such a ferrocene accelerator permits its use in mixture with microencapsulated anaerobic materials to provide highly desirable, rapid curing anaerobic adhesive systems. Obviously, many other advantageous uses of microencapsulated metallocenes will present themselves to those familiar with the art.

The urea-formaldehyde precondensates or oligomers useful in this invention may be derived in any of the ways described in the patents above cited. The molecular weight of these precondensates should be relatively low in order to avoid precipitation or premature polymerization. The ratio of urea to formaldehyde preferably will be in the range of about 0.9:1 to about 1.8:1 by weight, more preferably about 1.1:1 to about 1.5:1 by weight. It is also preferred that the formaldehyde be used in the form of an about 37% weight aqueous solution known as formalin since this is readily commercially available.

The starting point for the method of this invention is the preparation of an aqueous solution of a water-soluble precondensate of urea and formaldehyde. As used herein, the term "precondensate" is meant to include both the low molecular weight prepolymer of urea-formaldehyde and also any unreacted urea and formaldehyde which may remain. The concentration of the precondensate in the solution should be in the range of about 15 to about 50 percent by weight. Preferably, the concentration will be within the range of about 25 to about 35 percent by weight. The method of preparation of the precondensate is not critical and may be done in situ, if desired, by simply mixing urea and formaldehyde under reactive conditions of temperature and alkaline pH, as is well known in the art. Control of the molecular weight during this phase of the reaction will be by control of pH and temperature, as is also known in the art.

To the aqueous solution just described is added a particulate metallocene in such amount that the weight ratio of metallocene to precondensate is between about 1:1 and about 8:1. The particular ratio used is a matter of choice for any given application, but it will be recognized that the greater the amount of metallocene present, the thinner the resulting shell walls will be. In general, the preferred ratio will be in the range of about 1.1:1 to about 3:1 by weight. The metallocene will, of course, be added with good stirring in order to ensure the formation and retention of a relatively homogeneous dispersion or slurry. The particular size of the metallocene will be a matter of choice but should be sufficiently small (e.g., less than about 100 microns) to permit easy dispersion.

The key to the present invention is the addition, with stirring, to the slurry just described of a small amount of a cationic surfactant. The useful concentration range of the surfactant, expressed as a weight ratio to the metallocene, will usually be about 1:6,000 to about 1:10. Below this lower limit the beneficial effects of the surfactant are not realized to any significant extent, while above the upper limit the microcapsules become relatively difficult to separate and dry. The preferred range of ratios will ordinarily be about 1:5,000 to about 1:1,000. While the precise ratio chosen in any given case will, of course, depend upon the specific chemical compounds and conditions being used, the above ranges of ratios will be appropriate in most instances.

Without intending to be bound to any particular theory, it appears that the useful cationic surfactants will contain a polar atom, such as the nitrogen atom in a primary or secondary amine group. If this polarity limitation is met, the particular cationic surfactant used is a matter of routine experimentation and choice. While the preferred surfactants are not readily water-soluble, the over-all system would, of course, be simplified if a water-soluble surfactant were chosen; however, water solubility is not required, and the surfactant is preferably selected on the basis of its performance rather than its solubility. If a water-insoluble surfactant is used, its incorporation into the system may be facilitated by dissolving it in a suitable organic solvent, e.g., toluene or styrene. Naturally, the quantity of solvent used should be minimized since the system is basically aqueous. The preferred surfactants are the alkyl hydroxy amines, and their ethers, containing about 14–50 carbons, such as are sold under the trademark PRIMINOX by Rohm & Haas Co., Philadelphia, Pennsylvania. Especially preferred is the compound $t\text{-}C_{18\text{-}22}H_{37\text{-}45}NHCH_2CH_2OH$ sold under the trademark PRIMINOX T-1M.

The exact time of addition of the surfactant is not critical, provided only that it is added prior to commencing the urea-formaldehyde condensation polymerization and sufficient stirring time is provided to permit good dispersal of the surfactant throughout the liquid mass of the system. Thus, the surfactant may be added directly to the aqueous solution of the urea-formaldehyde precondensate or may be added after addition of the metallocene.

Following the slurrying of the metallocene in the surfactant/precondensate aqueous system, the urea-formaldehyde condensation polymerization is commenced, according to known procedures, by adjusting the pH of the system to the acid side by addition of a water-soluble acid. While any strong acid may be used, the water-soluble organic acids are preferred. Preferred acids include citric acid, formic acid, maleic acid and cyanoacetic acid. The pH should be maintained in the range of about 1 to about 6.5, preferably about 2 to about 3, during the polymerization period. The polymerization may be readily carried out at room temperature, i.e., about 20° C; however, the reaction may be speeded up and shell wall formation enhanced somewhat by moderate heating, e.g., at temperatures of about 35° –45° C. Usefully durable shell walls are obtained in about 1 hour of reaction at room temperature; however, improved properties are achieved if the room temperature reaction is allowed to proceed for a longer period, typically about 4 to about 8 hours, and longer reaction times may be used, if desired. Obviously, if elevated temperatures are used, the reaction may be completed in less time, the exact time required being a matter of choice and experimentation in any given system.

The reaction may be controlled and/or terminated in any known monomer, such as by adjusting the pH to the alkaline side, chilling the system, substantial dilution of the system with water, etc. While not essential to the success of the present process, it is often desirable to neutralize the system by addition of a base.

The resulting slurry may be stored or used as is, or the microcapsules may be separated, washed and dried by any ordinary technique, e.g., filtration, centrifugation, etc.

The following example is given by way of illustration only and is not intended to limit the invention in any way.

EXAMPLE

A mixture of 488.5 grams of a 37% by weight aqueous formaldehyde solution and 240 grams of urea was stirred and heated at 70° C. for one hour. The pH was adjusted to 8 with triethanolamine. One liter of water was added and the precondensate solution thus formed was allowed to cool to room temperature.

To 150 milliliters of above precondensate solution at room temperature were added, with good stirring, 50 grams of ferrocene. To this was added one milliliter of a 1% by weight solution of PRIMINOX T-1M in styrene and the mixture was stirred well. The pH was adjusted to 2.5 with a 10% by weight aqueous solution of citric acid. The reaction was allowed to proceed at room temperature, with good stirring, for about 50 minutes, at which time the mixture was thinned by addition of 50 milliliters of water. The reaction was continued for an additional 6 hours at room temperature, at which time 600 milliliters of water were added. The microencapsulated ferrocene thus formed was separated by filtration, was washed thoroughly with water, and the microcapsules were dried in an oven at low heat.

The microcapsules showed no sign of leakage during prolonged storage and were sufficiently durable to withstand normal handling but could be readily crushed upon application of localized pressure to release the ferrocene.

What is claimed is:

1. A process for microencapsulating a water-insoluble metallocene comprising:
   (a) providing an aqueous solution of a water-soluble precondensate of urea and formaldehyde wherein the precondensate concentration is about 15 to about 50 percent by weight;
   (b) adding to said precondensate solution a particulate metallocene in such amount that the weight ratio of metallocene to precondensate is between about 1:1 and about 8:1;

(c) adding to said precondensate solution or the mixture of said precondensate solution with said metallocene a cationic surfactant in such amount that the weight ratio of surfactant to metallocene is between about 1:6,000 and about 1:10 said surfactant having the formula t-$C_{18-22}H_{37-45}NHCH_2CH_2OH$ (d) forming a slurry of the metallocene;

(e) adjusting the pH of the resultant dispersion to about 1 to about 6.5 by addition of a water-soluble acid, thereby causing polymerization of said precondensate, and (f) continuing said polymerization in the temperature range of about 15° to about 80° C. until said metallocene particles are encapsulated with a shell of water-insoluble urea-formaldehyde polymer.

2. A process of claim 1 wherein the weight ratio of urea to formaldehyde in the precondensate is in the range of about 0.9:1 to about 1.8:1.

3. A process of claim 2 wherein the concentration of the precondensate in its aqueous solution is about 25 to about 35% by weight.

4. A process of claim 3 wherein the weight ratio of the metallocene to the precondensate is about 1.1:1 to about 3:1.

5. A process of claim 4 wherein the weight ratio of the cationic surfactant to the metallocene is about 1:5,000 to about 1:1,000.

6. A process of claim 5 wherein the pH is adjusted to about 2 to about 3.

7. A process of claim 6 wherein the polymerization is performed at a temperature of about 20° to about 45° C.

8. A process of claim 1 wherein the slurry is neutralized prior to recovery of the encapsulated metallocene particles.

9. A process of claim 1 wherein the metallocene is ferrocene.

* * * * *